United States Patent [19]

Camaggi et al.

[11] Patent Number: 5,268,383
[45] Date of Patent: Dec. 7, 1993

[54] HETEROCYCLIC DERIVATIVES OF ALKOXYACRYLATES WITH A FUNGICIDAL ACTIVITY

[75] Inventors: Giovanni Camaggi, Novara; Lucio Filippini, San Donato Milanese; Giovanni Meazza, Saronno; Raul Riva, Novara; Giampaolo Zanardi, Vigevano; Carlo Garavaglia, Cuggiono; Luigi Mirenna, Milan, all of Italy

[73] Assignee: Ministero Dell 'Universita' E Della Ricerca Scientifica E Technologica, Rome, Italy

[21] Appl. No.: 943,335

[22] Filed: Sep. 10, 1992

[30] Foreign Application Priority Data

Sep. 13, 1991 [IT]  Italy ................. MI91-A-002421

[51] Int. Cl.$^5$ ................. C07D 413/04; A61K 31/42
[52] U.S. Cl. ................. 514/378; 548/240; 548/245; 548/246
[58] Field of Search ................. 548/240, 245, 246; 514/378, 380

[56] References Cited

U.S. PATENT DOCUMENTS

| | | | |
|---|---|---|---|
| 3,631,169 | 12/1971 | Minami et al. | 548/245 |
| 4,397,853 | 8/1983 | Kawakita et al. | 514/378 |
| 4,883,807 | 11/1989 | Clough et al. | 514/427 |
| 5,156,669 | 10/1992 | Zierke et al. | 548/240 |

FOREIGN PATENT DOCUMENTS 273572  7/1988  European Pat. Off.

*Primary Examiner*—Mukund J. Shah
*Assistant Examiner*—Pavanaram K. Sripada
*Attorney, Agent, or Firm*—George P. Hoare, Jr.

[57] ABSTRACT

Heterocyclic derivatives with a fungicidal activity, for agricultural use, having the formula (I):

wherein:

A, B, D, are N, or =C—G;

G is H, halogen, $NO_2$, CN, —$COOR_5$, $C_1$–$C_6$ (halo)alkyl $R_1$, $R_2$ and $R_5$, are $C_1$–$C_6$ (halo)alkyl;

$R_3$ and $R_4$ are H, $C_1$–$C_2$ alkyl, —$COOR_6$, CN or a carbon-carbon bond;

$R_6$ is $C_1$–$C_6$ alkyl;

Y, W, are H, halogen, $C_1$–$C_6$ alkyls, phenyls, heterocycles.

11 Claims, No Drawings

HETEROCYCLIC DERIVATIVES OF ALKOXYACRYLATES WITH A FUNGICIDAL ACTIVITY

The present invention relates to heterocyclic derivatives of alkoxy acrylates having a high fungicidal activity, a process for their preparation and their use in agriculture.

The subject matter of the present invention are heterocyclic compounds having the general formula (I)

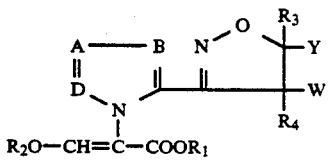

wherein:

A, B, D, either the same or different, represent a nitrogen atom, or a $=$C—G group;

G represents a hydrogen atom, a halogen atom, a nitro group, cyano group, a —COOR$_5$ group, a C$_1$–C$_6$ alkyl or C$_1$–C$_6$ haloalkyl group;

R$_1$, R$_2$ and R$_5$, the same or different, represent C$_1$–C$_6$ alkyl or C$_1$–C$_6$ haloalkyl groups;

R$_3$ and R$_4$, the same or different, each represents a hydrogen atom, a C$_1$–C$_2$ alkyl group, a —COOR$_6$ group, a cyano group, or jointly form a bond;

R$_6$ represents a C$_1$–C$_6$ alkyl group;

Y, W, the same or different, represent hydrogen, halogen, C$_1$–C$_6$ alkyls, phenyl, heterocycle with 5–6 atoms wherein the heteroatoms are O, N, S, said phenyl, heterocycle, or C$_1$–C$_6$ alkyls also being optionally substituted with halogens, C$_1$–C$_4$ alkyls or C$_1$–C$_4$ haloalkyls, C$_1$–C$_4$ alkoxyls or C$_1$–C$_4$ haloalkoxyls, phenyl groups, phenoxylic groups, heterocycloxylic groups or heterocycloxylicbenzocondensates optionally substituted.

Suitable substituents are, for example, halogens, trifluoromethyl, methoxyl, phenoxyl and pyridoxyl.

The structure of general formula (I) may have at least one E/Z isomerism.

The compounds having general formula (I) can be obtained by the addition of an aldoxymic compound having the formula (II):

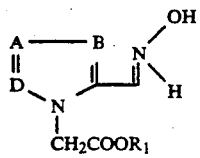

with an unsaturated compound having formula (III):

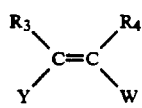

in the presence of a halogenating agent, such as sodium hypochlorite, chlorine, bromine, to obtain a compound having formula (IV)

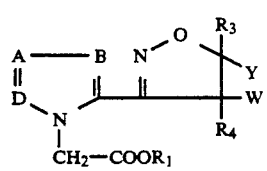

which is subsequently reacted with an alkyl formiate having formula (V):

 (V)

wherein R$_7$ represents a C$_1$–C$_3$ alkyl group, in a dipolar protic or aprotic solvent, in the presence of a base, at a temperature ranging from $-10°$ C. to 80° C., to obtain the salt of the compound having formula (VI):

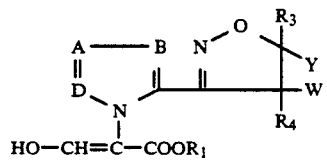

from which, by reaction with an R$_2$-X alkylating agent, wherein X represents a halogen atom (Cl, Br, I) or an activated ether, such as p-toluensulphonate, at a temperature ranging from $-10°$ C. to 80° C., the desired compound having formula (I) is obtained.

The compounds having formula (II) can be prepared by the reaction of (VII) with hydroxylamine hydrochloride in the presence of a base:

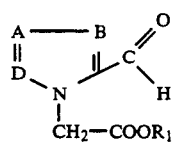

The compounds having formula (VII) can be prepared by treatment of the heterocyclic compounds having formula (VIII) with a suitable base:

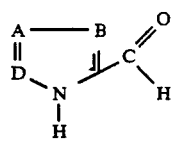

and an acetic ester having formula (IX):

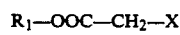

The compounds having the general formula (VIII) can be obtained with different processes, depending on the nature of A, B and D.

When A, B and D, represent a $=$C—G group, the compounds having formula (VIII) can be prepared according to the synthesis methods of pyrroles mentioned for example in "THE CHEMISTRY OF HETEROCYCLIC COMPOUNDS" vol. 48, part 1, R. A. JONES (Ed.), WILEY, 1990.

When A and D are both $=$N— and B represents a $=$C—G group, the compounds having formula (VIII)

can be prepared according to the methods for the synthesis of 1,2,3-triazoles mentioned for example in "THE CHEMISTRY OF HETEROCYCLIC COMPOUNDS", Vol. 39, J. A. MONTGOMERY (Ed.), WILEY, 1980.

When A and B are both =N— and D represents a =C—G group, the compounds having formula (VIII) can be prepared according to the methods for the synthesis of 1,2,4-triazoles mentioned for example in "THE CHEMISTRY OF HETEROCYCLIC COMPOUNDS" Vol 37, J. A. MONTGOMERY (Ed.), WILEY, 1981.

When A and D both represent =C—G groups and B is =N—, the compounds having formula (VIII) can be prepared according to the methods for the synthesis of imidazoles mentioned for example in "COMPREHENSIVE HETEROCYCLIC CHEMISTRY", Vol. 5, page 373, K. T. POTTS (Ed.), PERGAMON, 1984.

When A, B and D are =N—, the compounds having formula (VIII) can be prepared according to the methods for the synthesis of tetrazoles: D. MODERHACK, CHEM. BER. 1975, 108, 887; D. MODERHACK, CHEM. ZTG., 1977, 101, 403 (C.A. 1978, 88, 37706).

The compounds having formula (III) can be obtained with the methods known in the art.

When $R_3$ and $R_4$ jointly represent a carbon-carbon bond, these compounds can be prepared according to the methods for the synthesis of alkynes described, for example, in HOUBEN-WEYL "METHODEN DER ORGANISCHEN CHEMIE", Vol 5/2a, 1977; and L. BRANDSMA "PREPARATIVE ACETYLENIC CHEMISTRY", ELSEVIER PUBLISHING Co., 1971.

The compounds having formula (III) where $R_3$ and $R_4$ have one of the other meanings taken into consideration, can be prepared according to the methods for the synthesis of alkenes described, for example, in HOUBEN-WEYL "METHODEN DER ORGANISCHEN CHEMIE", Vol 5/1 b, 1972.

The compounds having general formula (I) have a particularly high fungicidal activity against phytopathogen fungi which attack cultivations of vines, cereals, Cocurbitacee and fruit trees.

Plant diseases which can be fought with the compounds of the present invention are, for example, the following:

Helminthosporium of cereals
*Plasmopara viticola* of vines
Phytium of vegetables
*Sphaerotheca fuliginea* of cucurbitacee (e.g. cucumbers)
Septoria of cereals
*Erysiphe graminis* of cereals
Rhynchosporium of cereals
*Podosphaera leucotricha* on apple trees
*Uncinula necator* on vines
*Venturia inequalis* on apple trees
Piricularia oryzae on rice
Botrytis cinerea
Fusarium on cereals The compounds having formula (I) are capable of carrying out a fungicidal activity which is both curative and preventive with limited or no phytotoxicity.

For practical use in agriculture it is often useful to have fungicidal compositions containing one or more compounds having formula (I), possibly also in isomeric form, as an active substance.

These compositions can be applied to all parts of the plant, for example, leaves, stems, branches and roots, or on the seeds, before planting, or also on the soil where the plant grows.

Compositions can be used in the form of dry powders, wettable powders, emulsionable concentrates, microemulsions, pastes, flakes, solutions, suspensions etc.: the choice of the type of composition depends on the specific use.

The compositions are prepared with the known methods, for example by diluting or dissolving the active substance with a solvent and/or solid diluent, possibly in the presence of surface-active agents.

The following can be used as solid diluents, or supports: silica, kaolin, bentonite, talc, infusorial earth, dolomite, calcium carbonate, magnesia, chalk, clays, synthetic silicates, attapulgite, sepiolite.

As liquid diluents, apart from water, naturally, it is possible to use various types of solvents, for example aromatics (xylenes or mixtures of alkylbenzols), chloro aromatics (chlorobenzol), paraffins (fractions of petroleum), alcohols (methanol, propanol, butanol, octanol), amines, amides (N,N'-dimethylformamide, N-methylpyrrolidone), ketones (cyclohexane, acetophenone, isophorone, ethylamylketone), esters (isobutyl acetate).

Surface-active agents which can be used are: salts of sodium, calcium or triethanolamine of alkylsulphates, alkylsulphonates, alkyl-arylsulphonates; polyethoxylated alkylphenols, fatty alcohols condensed with ethylene oxide, polyoxyethylated fatty acids, polyoxyethylated esters of sorbitol, ligninsulphonates.

The compositions may also contain special additives for specific purposes, for example tacking agents such as arabic rubber, polyvinylic alcohol, polyvinylpyrrolidone.

If desired, it is also possible to add other compatible active substances to the compositions of the present invention, such as fungicides, phytoregulators, antibiotics, weed-killers, insecticides, fertilizers.

The concentration of active substance in the above compositions can vary within a wide range, depending on the active compound, cultivation, pathogen, environmental conditions and type of formulation adopted.

The concentration of active substance generally varies from 0.1 to 95%, preferably from 0.5 to 90%.

The following examples illustrate the invention.

EXAMPLE 1

Preparation of (Z)-3-methoxy-2-{2-[5-(4-chlorophenyl)isooxazol-3-yl]pyrrol-1-yl} methyl acrylate (compound N.1)

0.32 g of 80% (w/w) sodium hydride in paraffin are dispersed in 10 cm³ of anhydrous DMF.

1.7 g of 2-{2-[5-(4-chlorophenyl)isooxazol-3-yl]pyrrol-1-yl}methyl acetate in 6.5 cm³ of ethyl formiate and 10 cm³ of anhydrous DMF are then added to the solution dropwise in 30'.

The mixture thus obtained is heated to 50° C. for 4 hrs.

It is cooled to 5° C. and 3.3 cm³ of CH₃I are added.

The mixture is kept at room temperature for 4 hrs, and is then diluted with water and extracted with ethyl acetate.

The organic phase is washed with brine, anhydrified on sodium sulphate and concentrated at reduced pressure.

The oil obtained is purified by silica gel chromatography, and eluated with hexane/ethyl acetate=8/2.

1.07 g of compound No.1 are obtained having m.p.=170°÷172° C. the structure being shown in Table 1 and NMR spectroscopic data in Table 2.

EXAMPLES 2-18

Using the same procedure described in Example 1, compounds 2-18 were prepared; the structure is shown in Table 1 and the respective NME spectroscopic data in Table 2.

EXAMPLE 19

Preparation of 2-{2-[5-(4-chlorophenyl)isooxazol-1-yl]pyrrol-1-yl}methyl acetate.

51 cm$^3$ of an aqueous solution of 7% HClO with 0.45 g of NaOH are added dropwise at 5°-10° C. into a solution of 5 g of 2-[(2-hydroxyiminomethyl)pyrrol-1-yl]methyl acetate and 7.5 g of 4-chlorophenylacetylene in 60 cm$^3$ of CH$_2$Cl$_2$.

The biphasic solution is left under vigorous stirring overnight at room temperature.

The organic phase is separated, and, after washing with brine, is anhydrified with Na$_2$SO$_4$ and concentrated at reduced pressure.

The crude product obtained is purified by silica gel chromatography, eluating with hexane/ethyl acetate=8/2.

1.7 g of the desire compound are obtained.

EXAMPLE 20

Preparation of 2-[(2-hydroxyiminomethyl)pyrrol-1-yl]-methyl acetate

A suspension of 30 g of 2-carboxyaldehyde-1-methoxy-carbonylmethylpyrrol, 18.1 g of hydroxylamine hydrochloride and 20.1 g of sodium acetate in 200 cm$^3$ of ethanol is stirred vigorously for 20 h at room temperature.

It is diluted with 500 cm$^3$ of water and the ethanol is distilled at reduced pressure.

The aqueous solution obtained is extracted with ethyl ether, which is subsequently washed with water, dried on Na$_2$SO$_4$ and concentrated at reduced pressure.

The oily crude product obtained (41 g) is purified by silica gel chromatography, eluating with the mixture hexane/ethyl acetate =85/15.

16.4 g of the desired compound are obtained as a light yellow solid.

EXAMPLE 21

Determination of the Preventive Fungicidal Activity Against Powdery Mildew of Cucumbers (*Sphaerotheca fuliginea* "Schlech" Salmon)

Cucumber plants cv. Marketer, grown in a vase in a conditioned environment, were sprayed on the lower faces of the leaves with the products under examination in a 20% hydroacetonic solution of acetone (v/v).

The plants were then kept in a conditioned environment for 1 day and were then sprayed on the upper faces of the leaves with an aqueous suspension of conidia of *Sphaerotheca fuliginea* (200000 conidia per cm$^3$).

The plants were then returned to a conditioned environment at 20° C. and 70% of relative humidity.

At the end of the incubation period of the fungus (8 days), the gravity of the infection was evaluated with indexes of an evaluation scale from 100 (=healthy plant) to 0 (=completely infected plant).

Compound No.3 showed a control of over 90, at a concentration of 500 ppm.

EXAMPLE 22

Determination of the Preventive Fungicidal Activity Against *Helminthosporium teres*

Barley leaves cv. Arna, grown in a vase in a conditioned environment, were sprayed on both faces with the products under examination in a 20% hydroacetonic solution in acetone (v/v).

After remaining 2 days in a conditioned environment at 20° C. and 70% of relative humidity, the plants were sprayed on both faces of the leaves with an aqueous suspension of conidia of *Helminthosporium teres* (250000 conidia per cm$^3$).

After remaining 24 h in an environment saturated with humidity, at 21° C., the plants were kept in a conditioned environment for the incubation of the fungus.

At the end of this period (12 days), the gravity of the infection was evaluated with indexes of an evaluation scale from 100 (=healthy plant) to 0 (=completely infected plant).

Using compounds 2 and 3 in a concentration of 500 ppm an index of over 90 was obtained.

EXAMPLE 23

Determination of the Curative Fungicidal Activity Against Vine Mildew (*Plasmopara viticola*) (B.et C.) (Berl et de Toni)

The leaves of the vine cv. Dolcetto, grown in a vase in a conditioned environment, at 25° C. and 60% of relative humidity, were sprayed on the lower face with an aqueous suspension of conidia of *Plasmopara viticola* (200000 conidia per cm$^3$).

After remaining 24 h in an environment saturated with humidity at 21° C., the plants were sprayed on both faces of the leaves with the products under examination in a 20% hydroacetonic solution of acetone (v/v).

At the end of the incubation period of the fungus (7 days), the gravity of the infection was evaluated with indexes of an evaluation scale from 100 (=healthy plant) to 0 (=completely infected).

Using compound No.3 in a concentration of 125 ppm an index =100 was obtained.

TABLE 1

| Compound | A | B | D | R1 | R2 | R3 | R4 | W | Y |
|---|---|---|---|---|---|---|---|---|---|
| 1 | H—C | H—C | H—C | CH$_3$ | CH$_3$ | B | B' | H | 4-chlorophenyl- |
| 2 | H—C | H—C | H—C | CH$_3$ | CH$_3$ | H | H | H | 4-chlorophenyl- |
| 3 | H—C | H—C | H—C | CH$_3$ | CH$_3$ | B | B' | H | t-butyl- |
| 4 | H—C | H—C | H—C | CH$_3$ | CH$_3$ | H | H | H | 4-methoxybenzyl- |
| 5 | H—C | H—C | H—C | CH$_3$ | CH$_3$ | B | B' | H | 3-trifluoromethylphenyl- |
| 6 | H—C | H—C | H—C | CH$_3$ | CH$_3$ | B | B' | H | methyl |
| 7 | H—C | H—C | H—C | CH$_3$ | CH$_3$ | B | B' | H | phenyl- |
| 8 | H—C | H—C | H—C | CH$_3$ | CH$_3$ | H | H | H | t-butyl- |
| 9 | H—C | H—C | H—C | CH$_3$ | CH$_3$ | B | B' | H | tiophen-2-yl- |

TABLE 1-continued

| Compound | A | B | D | R1 | R2 | R3 | R4 | W | Y |
|---|---|---|---|---|---|---|---|---|---|
| 10 | H—C | H—C | H—C | $CH_3$ | $CH_3$ | B | B' | H | 4-phenylphenyl- |
| 11 | H—C | H—C | H—C | $CH_3$ | $CH_3$ | B | B' | H | 2,4-dichlorophenoxymethyl- |
| 12 | H—C | H—C | H—C | $CH_3$ | $CH_3$ | H | H | H | 3-trifluoromethylphenoxymethyl- |
| 13 | H—C | H—C | H—C | $CH_3$ | $CH_3$ | B | B' | H | 4-fluorophenyl- |
| 14 | H—C | H—C | H—C | $CH_3$ | $CH_3$ | B | B' | H | 4-t-butylphenyl- |
| 15 | H—C | H—C | H—C | $CH_3$ | $CH_3$ | B | B' | H | 4-trifluoromethylphenyl- |
| 16 | H—C | H—C | H—C | $CH_3$ | $CH_3$ | B | B' | H | 4-cyanophenyl- |
| 17 | H—C | H—C | H—C | $CH_3$ | $CH_3$ | B | B' | H | 4-(2-trifluoromethoxy-1,1,2-trifluoroethoxy)phenyl- |
| 18 | H—C | H—C | H—C | $CH_3$ | $CH_3$ | B | B' | H | 2,4-dichlorophenyl- |

B = direct bond with R4
B' = direct bond with R3

TABLE 2

NMR 200 MHz ($CDCCl_3$) spectroscopic data

| Compound | |
|---|---|
| 1 | 3,7(3H)s, 3,9(3H)s, 6,4(1H)t, 6,63(1H)s, 6,7(2H)m 7,4(2H)dd, 7,6(1H)s, 7,7(2H)dd |
| 2 | 3,3(1H)s, 3,7(4H)m, 3,9(3H)s, 5,5(1H)m, 6,3(1H)m, 6,5(1H)m, 6,8(1H)m, 7,3(4H)m, 7,6(1H)s |
| 3 | 1,4(9H)s, 3,7(3H)s, 3,9(3H)s, 6,1(1H)s, 6,3(1H)s, 6,6(1H)m, 6,7(1H)m, 7,5(1H)s |
| 4 | 2,9(4H)m, 3,6(3H)s, 3,7(3H)s, 3,8(3H)s, 4,6(1H)m, 6,2(2H)m, 6,9(5H)m, 7,4(1H)s |
| 5 | 3,7(3H)s, 3,9(3H)s, 6,35(1H)m, 6,74(3H)m, 7,8(6H)m |
| 6 | 7.56(1H, s), 6.68(1H, dd), 6.61(1H, dd), 6.30(1H, dd), 6.07(1H, s), 3.83(3H, s), 3.68(3H, s), 2.36(3H, s). |
| 7 | 7,60(5H, m), 7.61(1H, s), 6.72(2H, m), 6.64(1H, s), 6.36(1H, dd), 3.87(3H, s), 3.72(3H, s). |
| 8 | 6.86(1H, s), 6.69(1H, dd), 6.38(1H, dd), 6.21(1H, dd), 4.23(1H, dd), 3.92(3H, s), 3.68(3H, s), 3.08(2H, m), 0.90(9H, s). |
| 9 | 7.60(1H, s), 7.48(1H, dd), 7.41(1H, dd), 7.10(1H, dd), 6.72(2H, m), 6.50(1H, s), 6.35(1H, dd), 3.86(3H, s), 3.71(3H, s). |
| 10 | 7.62(10H, m), 6.75(2H, m), 6.68(1H, s), 6.38(1H, dd), 3.88(3H, s), 3.73(3H, s). |
| 11 | 7.56(1H, s), 7.37(1H, d), 7.15(1H, dd), 6.90(1H, d), 6.71(1H, d), 6.66(1H, dd), 6.46(1H, s), 6.31(1H, dd), 5.14(2H, s), 3.82(3H, s), 3.68(3H, s). |
| 12 | 7.51(1H, s), 7.22(4H, m), 6.72(1H, dd), 6.49(1H, dd), 6.30(1H, dd), 4.92(1H, m), 4.05(2H, m), 3.86(3H, s), 3.72(3H, s), 3.35(2H, m). |
| 13 | 7.60(2H, m), 7.40(1H, s), 7.10(2H, t), 6.70(2H, m), 6.40(1H, t), 3.90(3H, s), 3.70(3H, s). |
| 14 | 7.70(2H, d), 7.60(1H, s), 7.50(2H, d), 6.70(2H, m), 6.60(1H, s), 6.40(1H, t), 3.90(3H, s), 3.70(3H, s), 1.40(9H, s). |
| 15 | 7.90(2H, d), 7.70(2H, d), 7.60(1H, s), 6.70(3H, m), 6.40(1H, t), 3.90(3H, s), 3.70(3H, s). |
| 16 | 7.90(2H, d), 7.70(2H, d), 7.60(1H, s), 6.70(3H, m), 6.30(1H, t), 3.90(3H, s), 3.70(3H, s). |
| 18 | 7.90(1H, d), 7.60(1H, s), 7.50(1H, d), 7.40(1H, q), 7.10(1H, s), 6.70(2H, m), 6.40(1H, t), 3.90(3H, s), 3.70(3H, s). |

We claim:

1. A heterocyclic derivative of an alkoxyacrylate which has fungicidal activity and has the formula:

(I)

wherein:

A, B and D are the same or different and each represents a nitrogen atom, or a =C—G group;

G represents a hydrogen atom, a halogen atom, a nitro group, a cyano group, a —$COOR_5$ group, a $C_1$-$C_6$ alkyl group of a $C_1$-$C_6$ haloalkyl group;

$R_1$, $R_2$ and $R_5$ are the same or different and each represents a $C_1$-$C_6$ alkyl group or $C_1$-$C_6$ haloalkyl group;

$R_3$ and $R_4$ are the same or different and each represents a hydrogen atom, a $C_1$-$C_2$ alkyl group, a —$COOR_6$ group, a cyano group or together form a carbon-carbon bond;

$R_6$ represents a $C_1$-$C_6$ alkyl group;

Y and W are the same or different and each represents a hydrogen atom, a halogen atom, a $C_1$-$C_6$ alkyl group, phenyl, said phenyl, $C_1$-$C_6$ alkyl group being optionally substituted with halogen, $C_1$-$C_4$ alkyl, $C_1$-$C_4$ haloalkyl, $C_1$-$C_4$ alkoxyl, $C_1$-$C_4$ haloalkoxyl, phenyl, and phenoxylic.

2. A heterocyclic derivative of an alkoxyacrylate according to claim 1, wherein:

A, B and D each represent =C—G, where G is a hydrogen atom;

$R_1$ and $R_2$ are $CH_3$;

$R_3$ and $R_4$ are each a hydrogen atom or jointly form a carbon-carbon bond;

W is a hydrogen atom;

Y is a $C_1$-$C_4$ haloalkyl substituted with phenyl and/or halogen, $C_1$-$C_6$ alkyl, or $C_1$-$C_4$ alkyl substituted with phenyl and/or alkoxy.

3. A heterocyclic derivative of an alkoxyacrylate according to claim 1 which is (Z)-3-methoxy-2-(2-[5-(4-chlorophenyl- isooxazol-3-yl]pyrrol-1-yl)methyl acrylate.

4. A heterocyclic derivative of an alkoxyacrylate according to claim 2 wherein $R_3$ and $R_4$ are each a hydrogen atom and Y is p-chlorophenyl.

5. A heterocyclic derivative of an alkoxyacrylate according to claim 2 wherein $R_3$ and $R_4$ from a carbon-carbon bond and Y is a tert-butyl group.

6. A heterocyclic derivative of an alkoxyacrylate according to claim 2 wherein $R_3$ and $R_4$ are each a hydrogen atom and Y is p-methoxybenzyl.

7. A heterocyclic derivative of an alkoxyacrylate according to claim 2 wherein $R_3$ and $R_4$ form a carbon-carbon bond, and Y is a m-trifluoromethylphenyl group.

8. A fungicidal composition comprising one or more of the derivatives according to claim 1 either alone or together with a solid support, liquid diluent, surface-active agent, or agriculturally active substance compatible therewith.

9. A method for fighting fungal infections comprising spraying a plant with one or more derivatives according to claim 1 either alone or in the presence of a solid support, liquid diluent, surface-active agent, or agriculturally active substance compatible therewith.

10. A fungicidal composition according to claim 8, wherein said agriculturally active substance is selected from fungicides, phytoregulators, antibiotics, weed-killers, insecticides and fertilizers.

11. A method according to claim 9 wherein the agriculturally active substance is selected from fungicides, phytoregulators, antibiotics, weed-killers, insecticides and fertilizers.

* * * * *